(12) United States Patent
Kortenbach et al.

(10) Patent No.: US 6,569,105 B1
(45) Date of Patent: May 27, 2003

(54) ROTATABLE AND DEFLECTABLE BIOPSY FORCEPS

(75) Inventors: Juergen A. Kortenbach, Miami Springs, FL (US); Saul Gottlieb, Miramar, FL (US); Kevin W. Smith, Coral Gables, FL (US); Charles R. Slater, Fort Lauderdale, FL (US); Thomas O. Bales, Coral Gables, FL (US)

(73) Assignee: Syntheon, LLC, Miami, FL (US)

( * ) Notice: Subject to any disclaimer, the term of this patent is extended or adjusted under 35 U.S.C. 154(b) by 0 days.

(21) Appl. No.: 09/661,593

(22) Filed: Sep. 14, 2000

(51) Int. Cl.[7] .............................................. A61B 10/00
(52) U.S. Cl. ........................................ 600/562; 606/167
(58) Field of Search ........................... 600/562, 564–567; 606/167, 170

(56) References Cited

U.S. PATENT DOCUMENTS

| 4,880,015 | A | | 11/1989 | Nierman | 128/751 |
|---|---|---|---|---|---|
| 5,354,297 | A | | 10/1994 | Avitall | 606/45 |
| 5,386,818 | A | | 2/1995 | Schneebaum | 128/4 |
| 5,439,478 | A | | 8/1995 | Palmer | 606/205 |
| 5,454,827 | A | | 10/1995 | Aust et al. | 606/170 |
| 5,618,294 | A | | 4/1997 | Aust et al. | 606/170 |
| 5,620,415 | A | | 4/1997 | Lucey et al. | 604/22 |
| 5,715,832 | A | | 2/1998 | Koblish | 128/754 |
| 5,885,288 | A | | 3/1999 | Aust et al. | 606/170 |
| 5,899,914 | A | | 5/1999 | Zirps et al. | 606/170 |
| 5,967,997 | A | * | 10/1999 | Turturro et al. | 600/567 |

* cited by examiner

*Primary Examiner*—Max F. Hindenburg
*Assistant Examiner*—Pamela Lynn Wingood
(74) *Attorney, Agent, or Firm*—David P. Gordon; David S. Jacobson; Thomas A. Gallagher

(57) ABSTRACT

An endoscopic or laparoscopic biopsy forceps instrument is provided which includes a flexible tubular member having proximal and distal ends, a biopsy jaw assembly at the distal end of the tubular member, an actuation assembly to operate the jaw assembly between open and closed positions, and a control assembly to deflect the biopsy jaw assembly relative to a lumen through which the instrument extends and to rotate the jaw assembly about the longitudinal axis of the instrument.

18 Claims, 6 Drawing Sheets

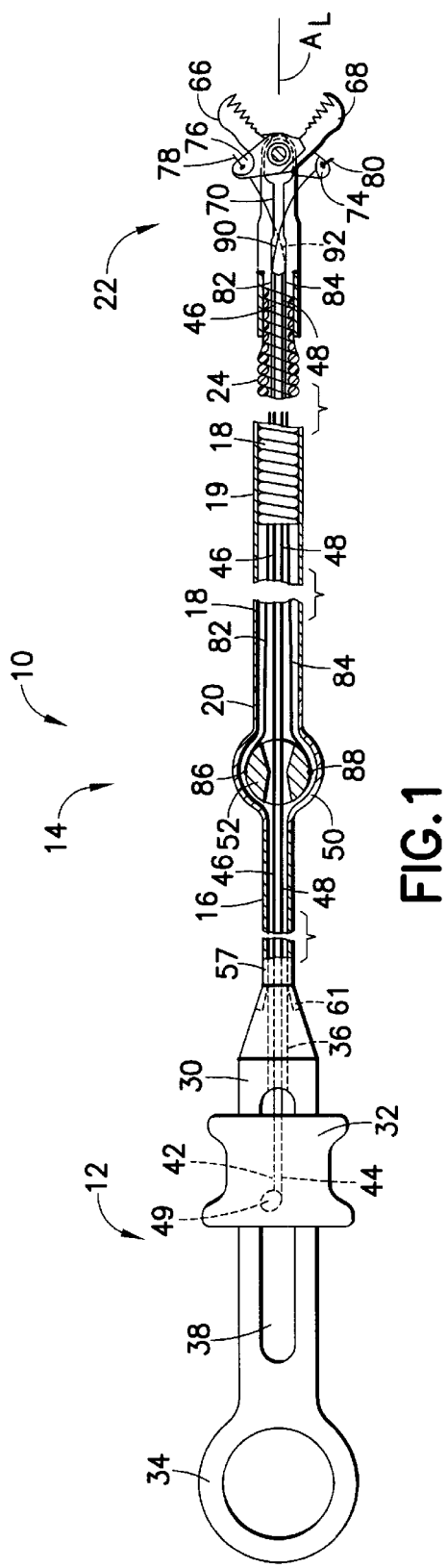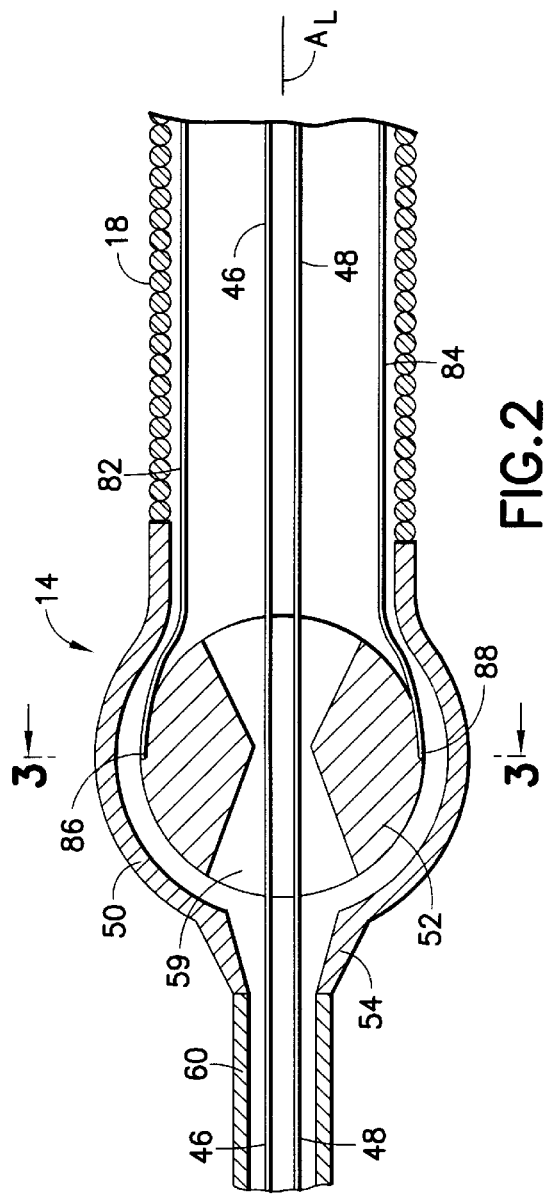
FIG. 1
FIG. 2

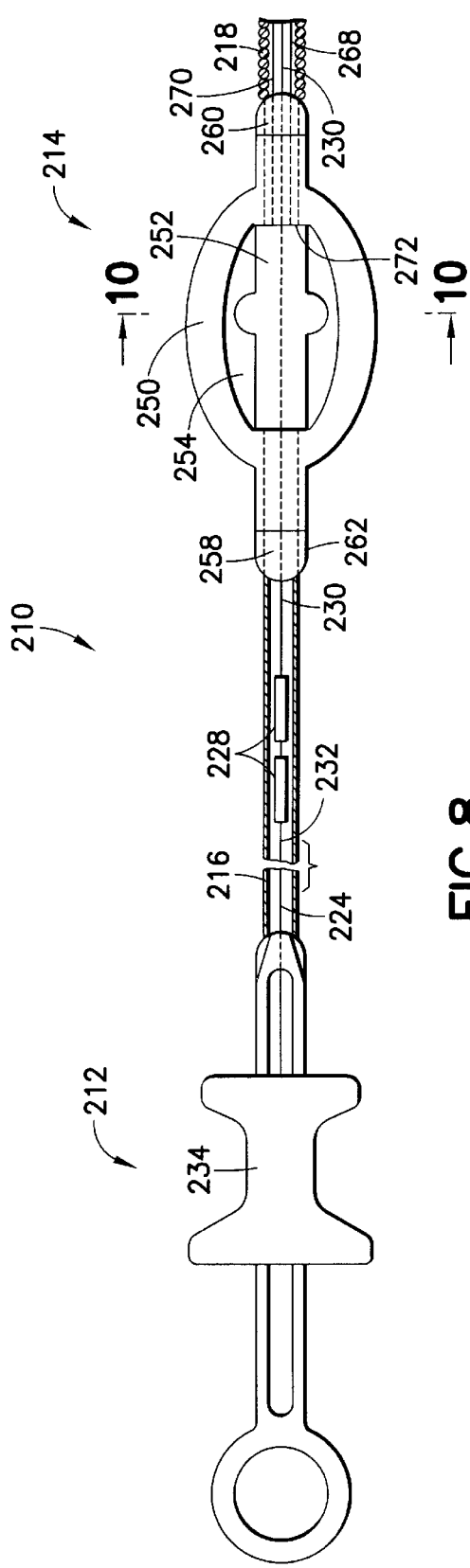
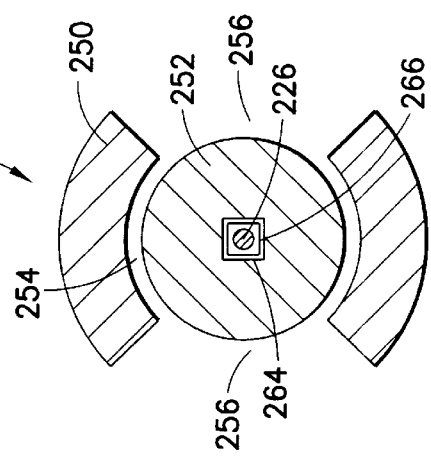
FIG. 8
FIG. 10

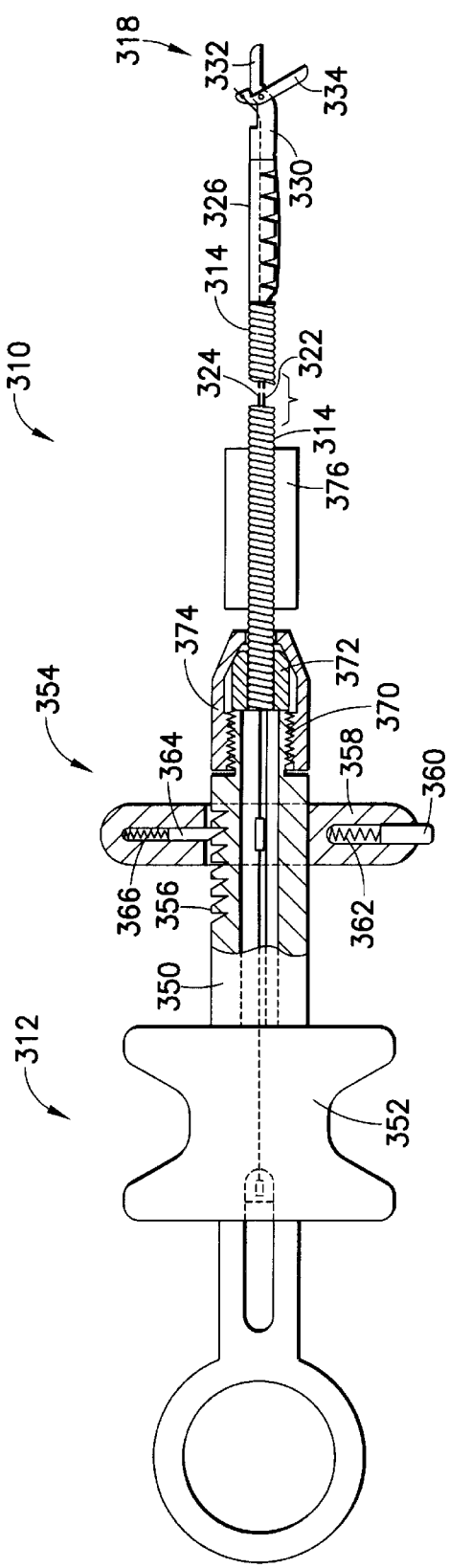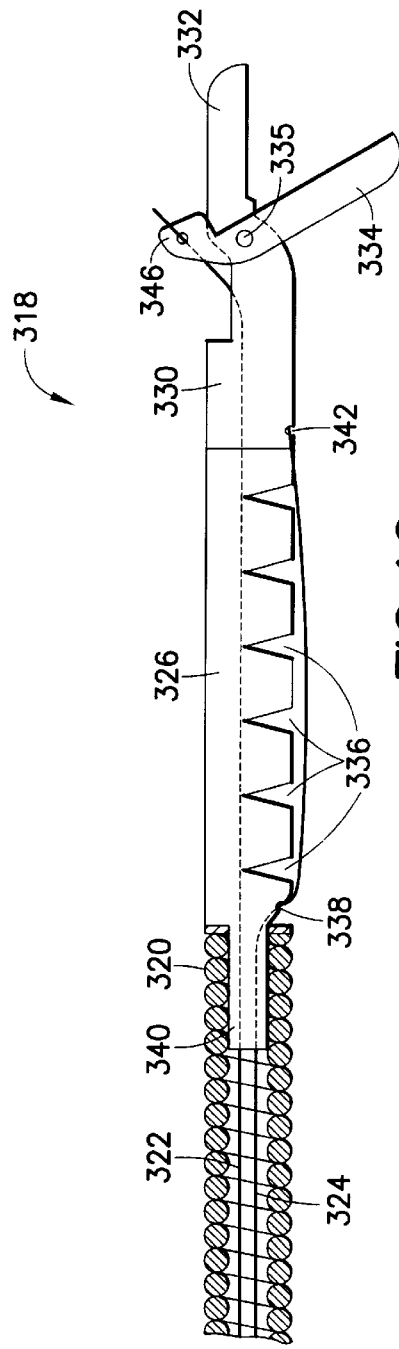

ROTATABLE AND DEFLECTABLE BIOPSY FORCEPS

BACKGROUND OF THE INVENTION

1. Field of the Invention

This invention relates broadly to surgical instruments. More particularly, this invention relates to biopsy forceps intended to be inserted through an endoscope or used in laparoscopic procedures.

2. State of the Art

Biopsy forceps are generally inserted through an endoscope and used to obtain tissue samples from within the body. It is often necessary to obtain a tissue sample from the wall or side of a biological lumen such as the esophagus. When using a conventional end-viewing endoscope, the distal end of the scope must be turned to the side to aim the instrument in the direction of the tissue to be sampled. However, the esophagus is quite narrow, making maneuvering of the endoscope within the lumen of the esophagus quite difficult. Although a side-viewing endoscope can be used to obtain an esophageal biopsy, the scope is nearly useless in examining the stomach which is also typically done in a procedure in which esophageal samples are desired, thus necessitating both an end-viewing endoscope and a side-viewing endoscope for a single procedure.

Accordingly, several biopsy forceps or similar devices have been described which enable deflection of the distal end of the biopsy forceps without requiring bending of the distal end of the endoscope. Such maneuvering permits samples to be taken off-axis from the endoscope lumen; i.e., "tangential" sampling.

For example, U.S. Pat. No. 5,715,832 to Koblish et al. discloses a deflectable biopsy forceps which utilizes a catheter-like shaft and a deflection wire coupled to the distal end of the shaft and extending along the length of the shaft. A pair of biopsy jaws are also coupled to the distal end of the shaft. When the deflection wire is tensioned, the shaft bends in the direction of the tension to direct the jaws radially and eventually up to 180°.

Another biopsy forceps device is disclosed in U.S. Pat. No. 5,386,818 to Schneebaum et al. The distal end of the Schneebaum device is spring biased to have a tendency to form an arcuate configuration. When the distal end of the device is substantially within the lumen of the endoscope, the biopsy jaws are directed substantially axially with the lumen of the endoscope. However, as the distal end is advanced from the lumen of the endoscope, an increasingly larger arcuate shape is provided.

U.S. Pat. No. 4,880,015 to Nierman discloses yet another biopsy forceps purportedly capable of tangential sampling. The biopsy forceps device has a hinge at a distal end thereof, and a jaw assembly is coupled to the device distal of the hinge. The jaw assembly is adapted to pivot, and thereby articulate, in one direction about the hinge to move the jaw assembly relative to the longitudinal axis of the device.

While each of the above described devices may have the ability to controllably deflect or bend to some degree or another, there is nevertheless no way to direct the deflection to sample a tissue at a particular location about the inner surface of the biological lumen. This is because the known devices are only capable of deflection in a single direction. That is, in the direction of the tension (Koblish et al.), the direction of the spring bias (Schneebaum), or the direction of pivot about a hinge (Nierman).

In addition, the desired direction of deflection cannot even be obtained by rotating the entire biopsy forceps within the lumen of the endoscope, due to the inability of the construct of biopsy forceps, in general, to controllably transmit rotational force, i.e., torque, along their relatively long lengths.

SUMMARY OF THE INVENTION

It is therefore an object of the invention to provide a biopsy forceps instrument which is optimized to sample esophageal tissue or tissue along the length of another biological lumen.

It is another object of the invention to provide a biopsy forceps instrument adapted to sample tissue at any rotational location about an end of the instrument and the end of an endoscope through which the instrument extends.

It is a further object of the invention to provide a biopsy forceps instrument having a deflectable end which can be controlled to move in any direction about the end of the instrument and the end of the endoscope.

It is an additional object of the invention to provide a biopsy forceps instrument which has a deflectable end and a rotatable jaw assembly.

In accord with these objects, which will be discussed in detail below, an endoscopic or laparoscopic biopsy forceps instrument is provided which includes a flexible tubular member having proximal and distal ends, a biopsy jaw assembly at the distal end of the tubular member, actuation means to operate the jaw assembly between open and closed positions, deflection means to deflect the biopsy jaw assembly relative to an endoscopic or laparoscopic lumen through which the instrument extends, and rotation means to rotate the distal end of the tubular member and jaw assembly about its longitudinal axis.

An endoscopic or laparoscopic biopsy forceps instrument is provided which includes a flexible tubular member having proximal and distal ends, a biopsy jaw assembly at the distal end of the tubular member, an actuation assembly to operate the jaw assembly between open and closed positions, and a control assembly to deflect the biopsy jaw assembly relative to a lumen through which the instrument extends and to rotate the jaw assembly about the longitudinal axis of the instrument.

According to a first embodiment, an actuation handle, e.g., of the conventional shaft and spool type, is provided to open and close the jaw assembly, and a control handle, preferably of ball and socket configuration, operates to direct (i.e., both rotate and move angularly relative to the longitudinal axis $A_L$ of the instrument) the jaw assembly via control wires coupled at one end to the ball and at the other end to the clevis of the jaw assembly such that tangential biting by the jaw assembly is facilitated. In the first embodiment, the jaws assembly includes two jaws positionable about the clevis, which in turn is rotatable relative to a coil. Actuation wires running from the actuation handle to the tangs of each jaw permit opening and closing of the jaw.

According to a second embodiment similar to the first embodiment, the jaw assembly includes two jaws, preferably made from a shape memory material and coupled together at their proximal ends, and a sleeve. Movement of the jaws relative to the sleeve, e.g., via coupling the proximal ends of the jaws to the actuation wire and fixing the sleeve at the distal end of the tubular member, operates to open and close the jaw assembly.

According to a third embodiment of the invention, the jaw assembly includes a proximal portion and a distal portion spring-biased relative to the proximal portion and thereby adapted to be deflected at a desired angle relative to the longitudinal axis of the instrument. However, the bias may be overcome when the instrument is forced through or withdrawn from an endoscope or lumen smaller than the radial extension of the distal portion of the jaw assembly. An actuation means is provided for operating the jaws, and a rotation control means is provided for rotating the jaw assembly.

According to fourth embodiment, the jaw assembly includes a flexible tube, a clevis terminating in a stationary jaw, and a jaw pivotably coupled to the clevis and thereby movable between open and closed positions relative to the stationary jaw. A proximal actuation means is provided to cause the movement. The flexible tube is preferably made from nitinol or another shape memory material, and preferably includes a plurality of slots oriented transverse the longitudinal axis of the tube which, under compressive force, are adapted to form the tube into a curved configuration. Once the compressive force is released, the shape memory property of the nitinol urges the tube back towards a linear configuration. A deflection wire in conjunction with the proximal actuation means is adapted to provide compressive force to the tube. In addition, a means is also provided to rotate the tube and the jaw assembly of the instrument.

In each of the embodiments, a biopsy forceps instrument is provided in which the jaw assembly is deflected or deflectable, the jaw assembly can be rotated about the longitudinal axis of the instrument, and the jaws can be operated to open and close to take a biopsy sample.

Additional objects and advantages of the invention will become apparent to those skilled in the art upon reference to the detailed description taken in conjunction with the provided figures.

BRIEF DESCRIPTION OF THE DRAWINGS

FIG. 1 is a broken partial section view of a first embodiment of a rotatable deflectable biopsy forceps instrument according to the invention;

FIG. 2 is an enlarged broken longitudinal section view of a distal control handle for controlling rotation and pitch of a biopsy jaw assembly according to the first embodiment of the invention;

FIG. 8 is a proximal handle portion of a rotatable deflecting biopsy forceps instrument according to a third embodiment of the invention;

FIG. 10 is a section view across line 10—10 in FIG. 8.

FIG. 11 is a broken partial section of a fourth embodiment of a rotatable deflecting biopsy forceps instrument according to the invention;

FIG. 12 is an enlarged broken section view of a biopsy forceps end effector according to the fourth embodiment of the invention.

DETAILED DESCRIPTION OF THE PREFERRED EMBODIMENTS

Figure 3:
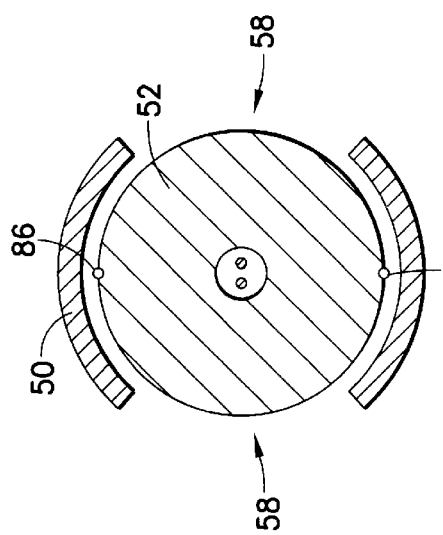
FIG. 3 is a view of a cross-section across line 3—3 in FIG. 2.

Turning now to FIG. 1, according to a first embodiment of the invention, a biopsy forceps surgical instrument 10 is shown. The instrument 10 includes a proximal actuation handle 12, a control handle 14 coupled to the actuation handle 12, a first tubular member 16 extending between the actuation handle 12 and the control handle 14, a second tubular member 18, e.g., a coil, preferably including a lubricous coating 19 such as PTFE or FEP, and attached to the distal end 20 of the control handle 14, and a biopsy forceps jaw assembly 22 coupled to the distal end 24 of the coil 18. The actuation handle 12 operates to open and close the jaw assembly 22, and the control handle 14 operates to direct (i.e., both rotate and move angularly relative to the longitudinal axis $A_L$ of the instrument).the jaw assembly such that tangential biting by the jaw assembly is facilitated.

The actuation handle 14 preferably includes a stationary member (shaft) 30 and a displaceable spool 32. The proximal end of the stationary member 30 is provided with a thumb ring 34 and a longitudinal bore 36 is provided at the distal end of the shaft. A longitudinal slot 38 extends from the proximal end of bore 36 to a point distal of the thumb ring 34. The proximal end 38 of the first tubular member 16 is coupled to the distal end of the bore 36 in the stationary member 30. The displaceable spool 32 is provided with a cross member (not shown) which passes through the slot 38 in the stationary member 30 and which secures the spool on the shaft. The proximal ends 42, 44 of two actuation wires 46, 48 are optionally rotatably coupled, e.g., with a swivel joint 49, to the spool, e.g., at the cross member. However, due to slack in the actuation wires 46, 48 a swivel is not essential.

Figure 3A:
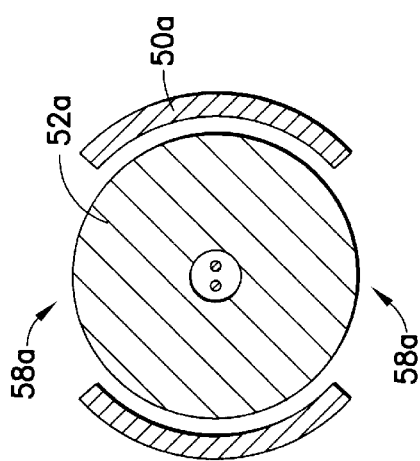
FIGS. 3a and 3b are views similar to FIG. 3 illustrating alternate sockets of the control handle of the first embodiment of the invention.
Figure 3B:
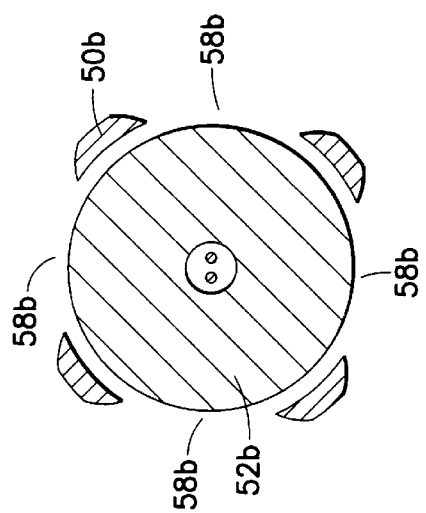

Referring to FIGS. 2 and 3, the control handle 14 includes a stationary socket 50 and a ball 52 movable within the socket. Each of the socket and ball are preferably formed from plastic. The socket 50 includes an axial port 54, and two side openings 58 which permit access to the ball such that the ball may be manually rotated within the socket about the longitudinal axis $A_L$ of the instrument and also may be rotated within the socket in directions other than about the longitudinal axis of the instrument. Referring to FIG. 3a, the openings 58a for accessing the ball 52a may alternatively be at the upper and lower portions of the socket 50a, or referring to FIG. 3b there may be more than two openings, e.g., four openings 58b, spaced about the socket for accessing the ball 52b. That is, the socket 50 may have any framework which permits manual access to the ball which facilitates movement of the ball 52, and preferably which also provides an element grippable by the physician. The ball 52 includes a preferably hourglass-shaped pathway 59 through which the actuation wires extend 46, 48 extend.

The first tubular member 16 is coupled at its proximal end 59 to the shaft of the actuation handle, e.g., with a flare nut connection 61 (FIG. 1), and at its distal end 60 to the rear port 54 of the socket 50, e.g., by gluing, a threaded connection, crimping, etc., and extends over the actuation wires 46, 48 to the proximal actuation handle 12. According to one embodiment of the invention, the tubular member 16 is relatively long, e.g., twelve to eighty inches, and preferably made from a flexible plastic. According to another embodiment of the invention, the tubular member 16 is relatively short, e.g., one-quarter inch to twelve inches, and preferably made from a relatively stiff material such as a substantially rigid plastic or metal.

Referring back to FIG. 1, the jaw assembly 22 preferably includes two jaws 66, 68 pivotally coupled to a clevis 70 which is in turn rotatably coupled via a bushing (not shown) to the distal end 24 of the coil 18, e.g., as shown in U.S. Pat. No. 5,439,478 to Palmer, which is hereby incorporated by reference herein in its entirety. Each jaw 66, 68 has a tang 74, 76 to which is coupled the distal end 78, 80 of an actuation wire 46, 48. As such, the actuation wires extend from spool 32 of the actuation handle 12, through the first tubular member 16, the axial port 54 of the socket, the pathway.59 through the ball, and the coil 18, and to the tangs 74, 76 of the jaw assembly 22. The jaw assembly 22 is described in more detail in U.S. Pat. No. 5,507,296, which is hereby incorporated by reference herein in its entirety. Movement of the spool relative to the shaft causes the jaws assembly 22 to open and close.

Figure 4:
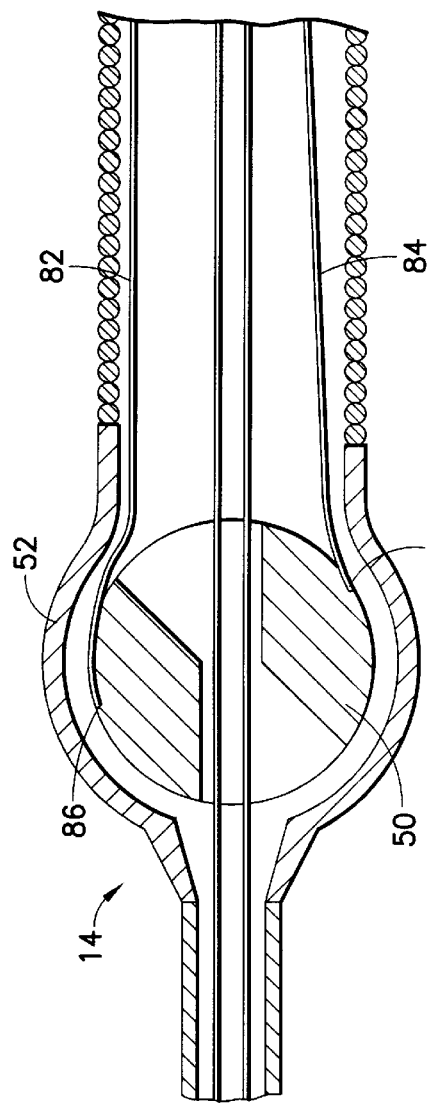
FIG. 4 is a view of similar to FIG. 2 showing the ball oriented with the socket of the control handle to deflect the jaw assembly.
Figure 5:
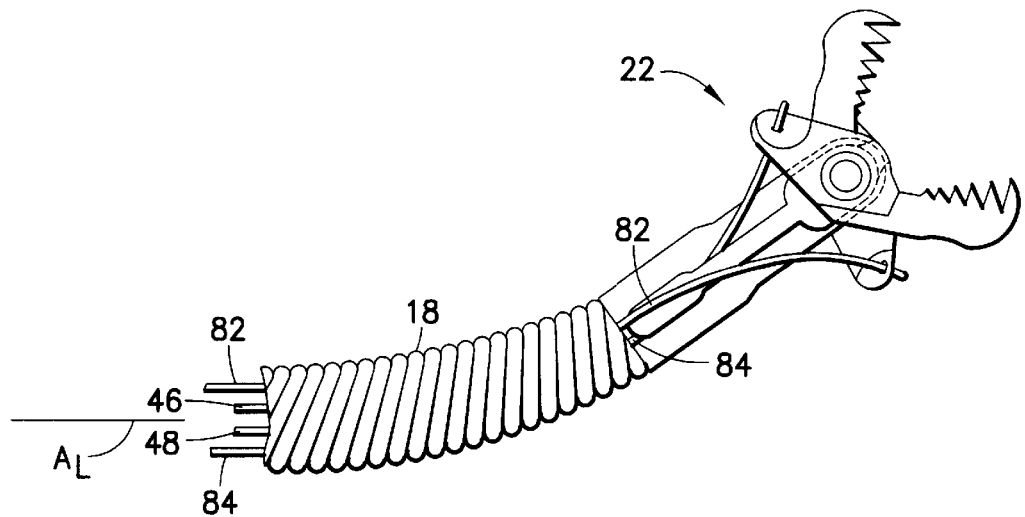
FIG. 5 is an enlarged side elevation of the distal end of the first embodiment of the invention showing the jaw deflected by the relative positions of the ball and socket in FIG. 4.

Referring again to FIGS. 2 and 3, two control wires 82, 84 extend from the ball 54 through the coil 18 to the jaw assembly 22. The control wires 82, 84 are preferably coupled at their proximal ends 86, 88 to the ball about a circumference oriented substantially perpendicular to axis $A_L$, and at their distal ends 90, 92 to upper and lower portions (or opposite sides) of the clevis 70 (or another stationary element at the distal end of the instrument), e.g., by welding. With the control wires arranged as stated, a non-axial movement of the ball 52 within the socket 50 (FIG. 4) results in displacement of the proximal ends 86, 88 of the control wires 82, 84 relative to each other such that the jaw assembly 22 is moved relative to the longitudinal axis $A_L$ of the instrument (FIG. 5), while rotation of the ball 52 relative to the socket 50 causes the jaw assembly 22 to rotate about the longitudinal axis $A_L$ and/or become biased or angled relative to the axis $A_L$.

In addition, by separating the actuation handle 12 from the control handle 14 simultaneous control of the instrument by a physician and an assistant is facilitated. For example, the physician may control rotation and deflection of the jaw assembly via the control handle, and the assistant may control opening and closing of the jaws via the actuation handle upon direction of the physician. However, where a single physician will operate the instrument, the actuation handle and control handle may be coupled directly together, or may be combined into a single handle assembly, in either instance eliminating the first tubular member 16.

Figure 6:
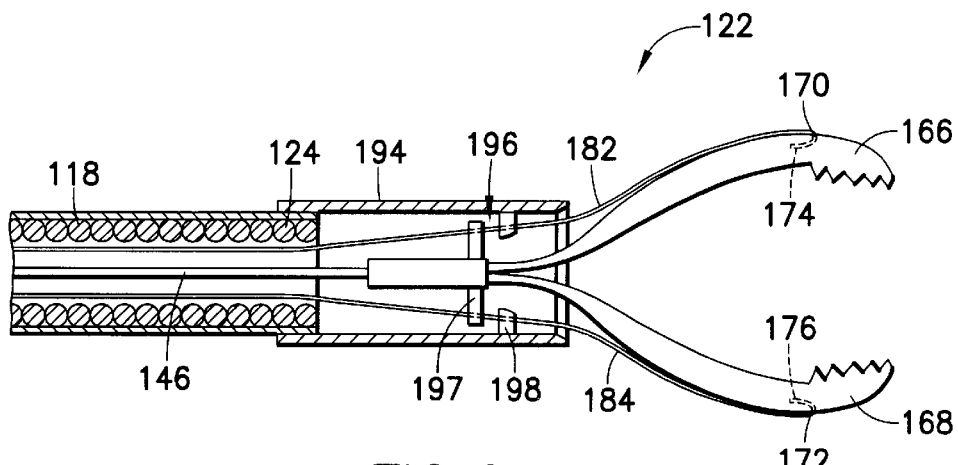
FIG. 6 is an enlarged broken section view of a biopsy forceps end effector according to a second embodiment of the invention, shown in a non-deflected configuration.
Figure 7:
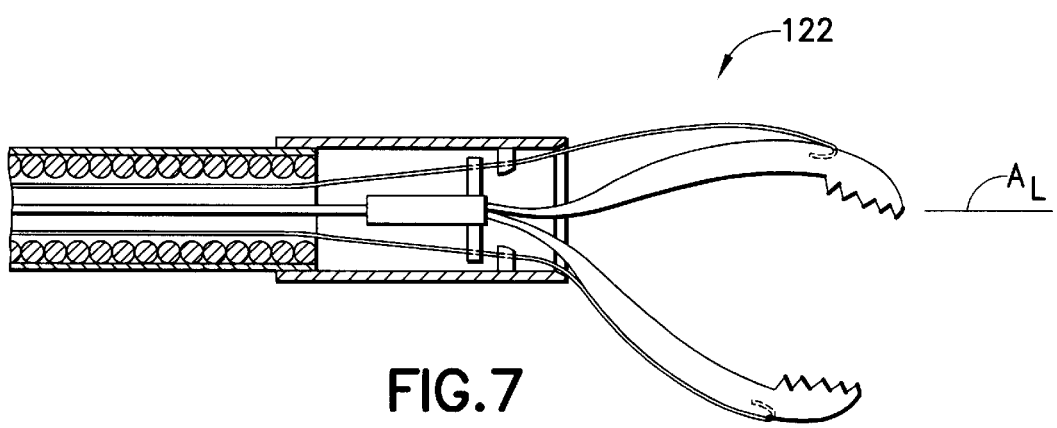
FIG. 7 is a view similar to FIG. 6 showing the biopsy forceps jaws in a deflected configuration.

Turning now to FIG. 6, according to a second embodiment of the invention, an instrument substantially similar to the first embodiment is provided with the following distinctions. First, a cylindrical sleeve 194 is rigidly coupled to the distal end 124 of the coil 118. Second, the jaw assembly 122 includes two jaws 166, 168 which are preferably integral with each other and preferably made from a shape memory alloy. The sleeve 194 and jaw assembly 122 are described in greater detail in U.S. Pat. Nos. 5,636,639 and 5,638,827, which are hereby incorporated by reference herein in their entireties. Third, each control wire 182, 184 is coupled at its distal end to a respective jaw 166, 168, e.g., by extending through holes 170, 172 and providing a bend 174,. 176 at the distal end of each control wire. Fourth, a single actuation wire 146 is used to operate the jaw assembly 122; i.e., move the jaw assembly proximally and distally relative to the cylindrical sleeve. Fifth, a stop 196 (including, e.g., a disk 197 at the proximal end of the jaw assembly 122 and a ring 198 at the distal end of the sleeve 194 and having an inner diameter smaller than the disk) is preferably provided to limit the distance that the jaw assembly 122 can be opened. The above distinctions provide a biopsy instrument which operates, from the physician's perspective, substantially the same as the first embodiment. That is, operation of the actuation handle opens and closes the jaw assembly, while operation of the control handle rotates and angularly deflects the jaw assembly (FIG. 7). More particularly, operation of the actuation handle causes the jaws to move relative to the sleeve, and when extended through the sleeve, permitted to open, and when retracted within the sleeve, forced closed. Referring to FIG. 7, manipulation of the ball within the socket of the control handle deflects the jaw assembly 122 relative to the longitudinal axis $A_L$.

Figure 9:
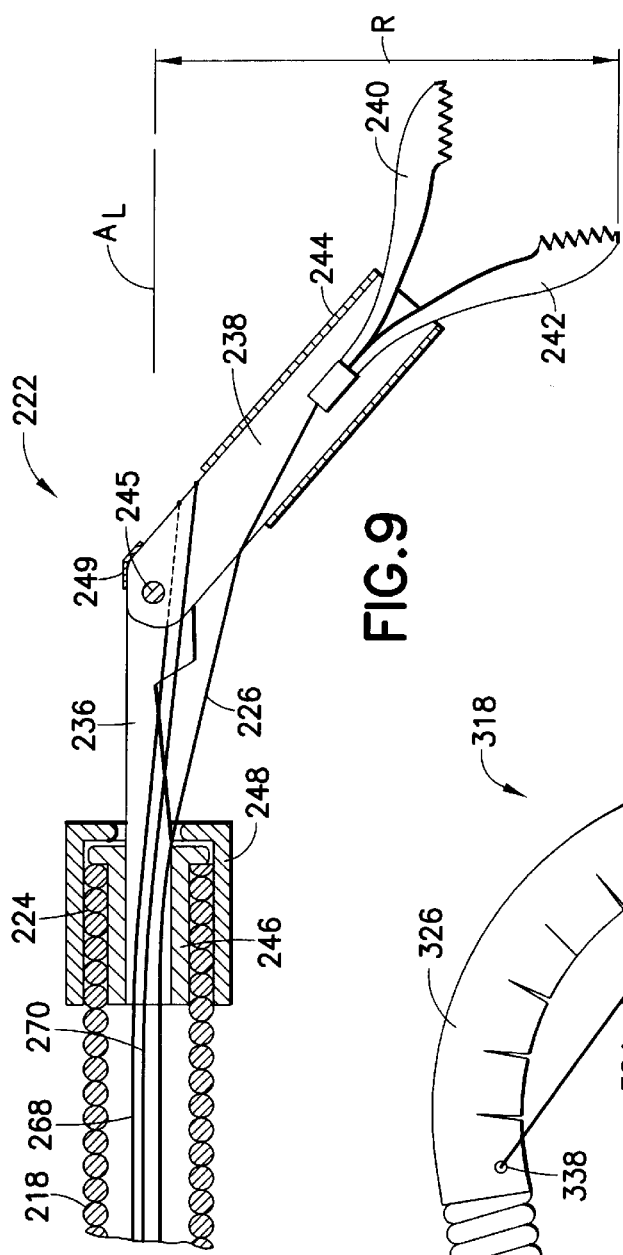
FIG. 9 is an enlarged broken section view of a deflected biopsy forceps end effector according to the third embodiment of the invention.

Referring now to FIGS. 8 and 9, a third embodiment of the biopsy forceps instrument 210 of the invention is shown. The instrument 210 includes a proximal actuation handle 212 similar to the first embodiment of the invention, a rotation control handle 214, a first tubular member 216 coupling the handles 212 and 214, and second tubular member or coil 218 distal of the control handle 214, and a jaw assembly 222 at the distal end 224 of the coil 218. An actuation shaft (wire) 226 extends from the actuation handle, through the first tubular member, the rotation handle, and the coil, and is coupled to the jaw assembly. The actuation shaft includes a swivel 228 permitting a distal portion 230 of the shaft to rotate freely relative to the proximal portion 232 of the shaft. Alternatively, the actuation shaft 226 is rotatably coupled to the spool 234 of the actuation handle as discussed with respect to the first embodiment of the invention.

The jaw assembly 222 includes a proximal portion 236 rotatably coupled to the coil 218, and a distal portion 238 including two jaws 240, 242 and a cylinder 244 which acts on the jaws when the jaws are moved relative thereto. The proximal and distal portions 236, 238 are coupled with a pivot pin 245. A means for rotatably coupling the proximal portion 236 to the coil 218 preferably includes a rotation collet 246 on the jaw assembly and a retaining sleeve 248 on the distal end 224 of the coil. The distal portion 238 is spring-biased by a spring portion 249 of cylinder 244 relative to the proximal portion 236 and thereby adapted to bend at a desired angle, e.g., 45° degrees, relative thereto. However, the bias may be overcome when the instrument 210 is forced through,an endoscope lumen with a radius smaller than the radial extension R of the distal portion 238 and withdrawing the instrument from the same.

Referring to FIG. 8, the control handle 214 includes a body 250 and a knob 252 mounted in the body, e.g., on bearings, in a manner which permits the knob to rotate coaxially relative to the body. The body 250 includes a central bore 254 with one or more apertures 256, a threaded proximal end 258, and a threaded distal end 260. The apertures 256 provide access to the knob 252, so that the knob can be rotated relative to the body, e.g., by a physician. The first tubular member 216 is connected to the threaded proximal end 258 of the body, e.g., by means of a flare-nut connection 262. The coil 218 is preferably similarly connected to the threaded distal end 260.

Referring to FIGS. 8 and 10, the knob 252 includes a non-circular bore 264, e.g., having the cross-sectional shape of a square. The knob 252 (for reasons discussed below) is preferably at least as long as the distance of movement required to open and close the jaw assembly 222. Referring to FIGS. 8–10, the distal portion 230 of the actuation shaft 226 extending through the bore 264 of the knob is provided with a key 266; that is, a spline element fixed on and about the shaft or, alternatively, rigidly and fixedly interposed between two portions of the shaft. The key 266 preferably has a rectangular shape but may have another non-circular shape. The key 266 is slidably axially movable within the bore. Therefore, the shaft 226 may be moved axially through the bore 264 (and that is why the length of the knob is preferably at least as long as the distance of movement required to open and close the snare). However, when the knob 252 is rotated relative to the body 250, the key 266 within the bore 264 is rotated and, consequently, the shaft 226 (distal of the swivel 228) and jaw assembly 222, at the distal end thereof, are rotated about the longitudinal axis $A_L$ of the instrument. Alternatively, no key is required, as the longitudinal displacement necessary to open and close the jaw assembly is quite small. As such, the actuation shaft 266 can be fixed within the knob 252 and the knob can be configured to move within the handle 250 the necessary longitudinal displacement.

In addition, preferably two control wires 268, 270 are fixed at the distal end 272 of the knob 252 and extend through the coil 218 where they are fixed to one or more locations on the jaw assembly 222, and preferably,.to the distal portion 238 of the jaw assembly.

In operation, when the distal end of the instrument 210 is extended beyond the lumen of an endoscope, the jaw assembly 222 naturally assumes an angled (or "deflected") state. The orientation of the deflection may then may adjusted by operation of the rotation control handle 214 such that the actuation shaft 226 and control wires 268, 270 all operate to torque the jaw assembly 222 in a rotational manner. To that effect, the key 266 on the actuation shaft 226 and the interfering bore 264 of the knob 252 provide rotational control to the actuation shaft 226, while the control wires 268, 270, fixed to the distal end of the knob are controllably rotated -by rotation of the knob to, in turn, also apply rotational forces to the jaw assembly.

Figure 13:
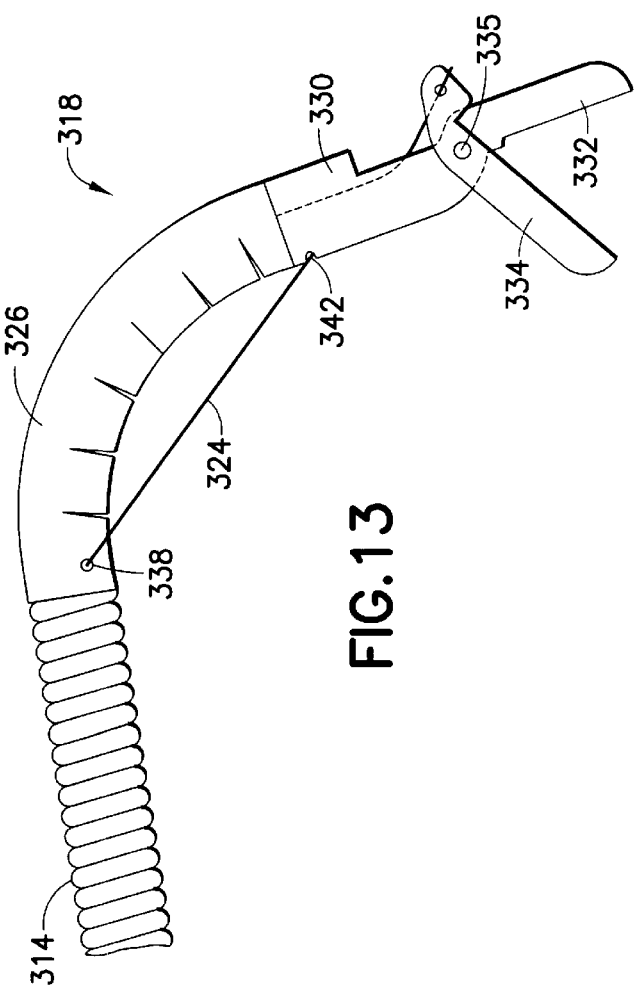
FIG. 13 is an enlarged perspective view of the biopsy forceps end effector of FIG. 11 shown in a deflected configuration.

Turning now to FIGS. 11–13, a fourth embodiment of a biopsy forceps instrument 310 according to the invention is shown. The instrument 310 includes a proximal actuation handle 312, a coil 314 rotatably coupled to the distal end of the handle 312, and a jaw assembly 318 at the distal end 320 of the coil 318. A jaw actuation wire 322, as well as a deflection wire 324 extend from the actuation handle 312, through the coil 318, and are coupled to the jaw assembly 318, as described below.

More particularly, the jaw assembly 318 includes a flexible, preferably nitinol tube 326, a clevis 330 at the distal end of the nitinol tube and terminating in a stationary jaw 332, and a rotatable jaw 334 rotatably coupled to the clevis, e.g., via a pin 335, such that the rotatable jaw 334 may pivot relative to the stationary jaw between open and closed positions. The nitinol tube 326 is provided with a plurality of preferably sector-shaped slots 336 oriented transverse the longitudinal axis of the tube. The slots 336 permits the nitinol tube 326 to be forced upon itself into a curved configuration, while the shape memory property of the nitinol urges the tube towards a linear configuration. The tube 326 also includes a proximal radial hole 338 on the side of the tube including the slots 336. In addition, the tube 326 is preferably fixedly coupled to the distal end 320 of the coil 318; for example, the proximal end of the tube may be provided with a decreased diameter portion 340 which is interference fit with the distal end of the coil 318. The clevis 330 also includes a radial hole 342 at preferably the same radial orientation as the radial hole 338 of the tube 326. The actuation wire 322 extends through the tube 326 and the clevis 330, exits through an opening 344 in the clevis, and is coupled to a tang 346 of the rotatable jaw 334. The deflection wire 326 extends into the tube and then out the radial hole 338 of the tube and then preferably into the radial hole 342 of the clevis, where the deflection wire is coupled to the clevis, e.g., by soldering, welding, crimping, etc. Alternatively, no radial hole in the clevis is required, and the distal end of the deflection wire may be coupled to the outer surface of the clevis.

Referring particularly to FIG. 11, the actuation handle 312 includes a stationary member 350, an actuation spool 352 slidable on the stationary member and to which the actuation wire 322 is coupled, and a rack assembly 354 including a rack 356 along the stationary member 350 and a pawl spool 358 which releasably engages the stationary member and to which the deflection wire 324 is coupled. The pawl spool 358 includes a push button 360, a first spring 362 biasing the push button outward, a pawl bar 364 engaging the rack 356, a second spring 366 biasing the pawl bar towards the rack, and a link (not shown) which couples the push button 360 to the pawl bar 364. When the push button is pushed to compress the first spring 362, the pawl bar 364 is moved against the second spring 366 and is released from the rack such that the pawl spool 358, may be moved along the rack. When the push button 360 is then released, the pawl spool 358 is engaged in another position along the length of the stationary member. Linear movement of the pawl spool 358 causes like linear movement of the distal end of the deflection wire 324, which is coupled to the jaw assembly.

The distal end of the stationary member 350 is rotatably coupled to the coil 318. According to a one exemplar coupling, the distal end of the stationary member includes threads 370. The proximal end of the coil is provided with a preferably frustoconical element 372 fixedly secured about the coil. A nut 374 extends over the element 372 and is threadably coupled to the stationary member 350 such that the element is permitted to rotate within the nut. A finger grip 376 is preferably provided about a proximal portion of the coil 318 to facilitate rotation of the coil relative to the stationary member 350. Alternatively, the instrument 310 can be configured to effect rotation between the coil 318 and the tube 326 or between the tube 326 and the clevis 330.

In operation, rotation of the coil 318 relative to the stationary member 350 causes the jaw assembly to rotate about the longitudinal axis $A_L$ of the instrument. Movement of the pawl spool 352 along the rack of the stationary member 350 causes angular deflection of the nitinol tube 326 and thereby the jaws 332, 334 (FIG. 13)(via relative proximal movement of the pawl spool) or straightening (via relative distal movement) of the jaw assembly. Movement of the actuation spool along the stationary member operates to open and close the jaws of the jaw assembly.

In each of the embodiments, a biopsy forceps instrument is provided in which the jaw assembly is deflected or deflectable, the jaw assembly can be rotated about the longitudinal axis of the instrument, and the jaws can be operated to open and close to take a biopsy sample.

There have been described and illustrated herein several embodiments of a rotatable and deflectable biopsy forceps instrument. While particular embodiments of the invention have been described, it is not intended that the invention be limited thereto, as it is intended that the invention be as broad in scope as the art will allow and that the specification be read likewise. Thus, while particular jaw assemblies have been disclosed, it will be appreciated that other jaw assemblies can be used as well. In addition, while particular types of actuation handles, e.g., a shaft and spool, have been disclosed, it will be understood that other actuation handle assemblies known in the art for opening and closing a jaw assembly can be used as well. Further, wherever a tubular member is described between the actuation handle and the control handle, it will be appreciated that the tubular member may be eliminated and that the control handle may be coupled directly to the actuation handle, or that the control and actuation handles may be integrated into a single handle. Also, while several means for permitting a distal portion of an actuation wire (or shaft) to rotate relative to the actuation handle has been disclosed, it will be recognized that other mechanisms may be used as well. Furthermore, while it is preferred that a coil be used for the tubular member to which the jaw assembly is coupled, it will be understood that other tubular members may be used as well. Moreover, where two control wires for rotating the jaw assembly have been disclosed, it will be appreciated that more than two wires may be used as well. Also, where a nitinol shape memory material is described, it will be appreciated that, as an alternative, other flexible or other shape memory materials known in the art may be used. Furthermore, where a slotted shape memory tube is stated to be part of a jaw assembly, it will be appreciated that the tubular member (coil) may be configured to include a transversely slotted distal portion to function as described. Moreover, while in the fourth embodiment a deflection wire is described as being coupled to the clevis of a jaw assembly, it will be appreciated that the deflection wire may alternatively be coupled to the distal end of the shape memory tube. In addition, where an axially movable jaw assembly is disclosed in conjunction with a fixed closing sleeve, the jaw assembly may be fixed and the sleeve may be coupled to the actuation wire to be moved relative to the jaw assembly to accomplish opening and closing of the jaws. Also, while an exemplar stop mechanism has been described with respect to the previously discussed jaw assembly, other stop mechanisms may be used. Furthermore, any described couplings can be different than that described, provided the components and assemblies operate relative to each other as required. Moreover, while a preferred ratchet assembly for operating deflection of the jaw assembly of the fourth embodiment has been disclosed, other mechanisms accomplishing the same may be used. In addition, wherever an endoscopic instrument is discussed, it will be appreciated that the same applies to a laparoscopic instrument or any instrument designed to be inserted into the human body through any medical scope device or otherwise. It will therefore be appreciated by those skilled in the art that yet other modifications could be made to the provided invention without deviating from its spirit and scope as claimed.

What is claimed is:

1. A biopsy forceps instrument having a longitudinal axis, comprising:
    a) a flexible tubular member having proximal and distal ends;
    b) a biopsy jaw assembly including at least two jaws at said distal end of said tubular member;
    c) an actuation means to operate the jaw assembly between open and closed positions, said actuation means including an actuation handle and an actuation wire coupled to said actuation handle and extending through said tubular member, and being coupled to said jaw assembly, wherein operation of said actuation handle causes said actuation wire to move longitudinally within said tubular member to effectuate opening and closing of said jaws; and
    d) control means for rotating said biopsy jaw assembly about and for deflecting said biopsy jaw assembly relative to the longitudinal axis of said instrument.

2. A biopsy forceps instrument according to claim 1, wherein:
    said actuation handle includes a stationary member, and a movable member movable relative to said stationary member, said stationary member including a distal bore in communication with an interior of said tubular member, and said actuation wire being coupled to said movable member.

3. A biopsy forceps instrument according to claim 2, wherein:
    said actuation wire includes a distal end which is adapted to swivel relative to said movable member.

4. A biopsy forceps instrument according to claim 1, wherein:
    said control means includes a socket, a ball rotatable within and relative to said socket, and at least one control element coupled to said jaw assembly, said socket coupled to said stationary member, and said ball fixedly coupled to said at least one control element,
    wherein said ball is rotatable relative to said socket about the longitudinal axis, and also in a direction other than about the longitudinal axis.

5. A biopsy forceps instrument according to claim 1, wherein:
    said tubular member is a coil.

6. A biopsy forceps instrument according to claim 1, wherein:
    said jaw assembly includes a clevis, first and second jaws coupled to said clevis, at least one of said first and second jaws being rotatable relative to the other, and said clevis being coupled to said distal end of said tubular member.

7. A biopsy forceps instrument according to claim 6, wherein:
    each of said jaws rotatable relative to the other includes a tang, and said actuation means comprises an actuation wire coupled to said tang.

8. A biopsy forceps instrument according to claim 1, wherein:
    said jaw assembly includes a plurality of jaws made from a shape memory material, and a tubular sleeve extending over at least a proximal portion of said jaws,
    at least one of said jaws and said tubular sleeve being movable relative to the other such that when said tubular sleeve is positioned over said jaws at a first location, said jaws are forced into a closed position, and when said tubular member is at least partially withdrawn relative to said jaws, said jaws are permitted to attain an open position.

9. A biopsy forceps instrument according to claim 1, further comprising:
    e) a second tubular member extending between said actuation means and said control means.

10. A biopsy forceps instrument according to claim 1, wherein:
    said actuation means and said control means are provided in a common handle assembly.

11. A biopsy forceps instrument having a longitudinal axis, comprising:
    a) an actuation handle having a stationary member and a movable member movable relative to said stationary member, said stationary member having a distal end;

b) a first tubular portion having a proximal end and a distal end, said proximal end rotatably coupled to said distal end of said actuation handle;

c) a second tubular portion provided with a plurality of axially transverse slots permitting said tubular portion to be bent about said slots into a curved configuration when subject to a compressive force;

d) a jaw assembly including two jaws, at least one of said jaws being rotatable relative to said other, said jaw assembly coupled to said distal end of said second tubular portion;

e) a jaw actuation wire coupled between said movable member and said jaw assembly, wherein movement of said movable member relative to said stationary member causes said actuation wire to move longitudinally within said tubular member and cause said jaws to move between open and closed positions;

f) a deflection means for bending said second tubular portion about said slots such that the jaw assembly at the distal end of said second tubular portion is deflected relative to the longitudinal axis of said instrument; and g) means for rotating said jaw assembly axially about the longitudinal axis.

12. A biopsy forceps instrument according to claim 1, wherein:

said second tubular portion is a shape memory tube.

13. A biopsy forceps instrument according to claim 12, wherein:

said second tubular portion is a nickel-titanium tube.

14. A biopsy forceps instrument according to claim 12, wherein:

said slots in said second tubular portion a substantially sector shaped.

15. A biopsy forceps instrument according to claim 12, wherein:

said second tubular portion assumes a substantially linear configuration when said compressive force is released.

16. A biopsy forceps instrument according to claim 12, wherein:

said deflection means includes a deflection wire having proximal and distal ends, said distal end coupled to one of distal portion of said second tubular member and said jaw assembly, and said proximal end coupled to a mechanism which releasably secures said proximal end of said deflection wire at a number of discrete longitudinal locations relative to the longitudinal axis of said instrument.

17. A biopsy forceps instrument according to claim 16, wherein:

said deflection wire extends outside a portion of said second tubular portion.

18. A biopsy forceps instrument according to claim 16, wherein:

said mechanism includes a rack and a pawl spool, said rack provided on said stationary member, and said pawl spool being releasably lockable relative to said rack.

* * * * *